(12) United States Patent
Kumar et al.

(10) Patent No.: US 7,267,837 B2
(45) Date of Patent: Sep. 11, 2007

(54) ENZYME ELECTRODE AND PROCESS FOR PREPARATION THEREOF

(76) Inventors: Arun Kumar, National Physical Laboratory, Dr. K. S. Krishnan Marg., New Delhi (IN) 110 012; Rajesh, IPMD - CSIR, 14 Satsang Vihar Marg., New Delhi (IN) 110 067; Bansi Dhar Malhotra, National Physical Laboratory, Dr. K. S. Krishnan Marg., New Delhi (IN) 110 012

( * ) Notice: Subject to any disclaimer, the term of this patent is extended or adjusted under 35 U.S.C. 154(b) by 305 days.

(21) Appl. No.: 10/345,163

(22) Filed: Jan. 16, 2003

(65) Prior Publication Data

US 2004/0149577 A1 Aug. 5, 2004

(51) Int. Cl.
*B05D 3/00* (2006.01)
*G01N 27/327* (2006.01)
(52) U.S. Cl. .................. 427/2.13; 204/403.14
(58) Field of Classification Search .......... 204/403.04, 204/403.05, 403.09, 403.01, 403.14; 205/777.5, 205/778; 427/2.11, 2.13
See application file for complete search history.

(56) References Cited

U.S. PATENT DOCUMENTS 6,458,296 B1 10/2002 Brandenberger ............... 264/9

FOREIGN PATENT DOCUMENTS

| EP | 0368209 A | 5/1990 |
|----|-----------|--------|
| EP | 0771867 A | 5/1997 |
| EP | WO99 19507 | 4/1999 |

OTHER PUBLICATIONS

Brahim et al. ("Amperometric determination of cholesterol in serum using a biosensor of cholesterol oxidase contained within a polypyrrole-hydrogel membrane," Analytica Chimica Acta 448 (2001) 27-36).*
Niu et al. ("Reagentless mediated biosensors based on polyelectrolyte and sol-gel derived silica matrix," Sensors and Actuators B 82 (2002) 250-258).*
CAPLUS abstract of Dong (CN 1118376 A).*
CAPLUS abstract of Watanabe et al. (WO 2002057767 A1).*
CAPLUS abstract of Li et al. ("Polyaniline/Prussian blue composite film electrochemical biosensors for cholesterol detection," Chinese Journal of Chemistry (2002), 20(10), 1038-1043).*

(Continued)

*Primary Examiner*—Alex Noguerola
(74) *Attorney, Agent, or Firm*—Nixon & Vanderhye P.C.

(57) ABSTRACT

The present invention relates to an enzyme electrode useful for estimation of cholesterol in aqueous medium, said electrode comprising:
  i. an electrically conductive base plate,
  ii. a film of sol gel derived material deposited thereon,
said sol gel derived material of step b) being microencapsulated cholesterol oxidase with an electron mediator. The present invention also relates to a process for the preparation of an enzyme electrode by coating an immobilized cholesterol oxidase (ChOx) and mediator on a silicate sol gel by microencapsulation.

8 Claims, 1 Drawing Sheet

Concentration of cholesterol in mM

OTHER PUBLICATIONS

Figure 1:
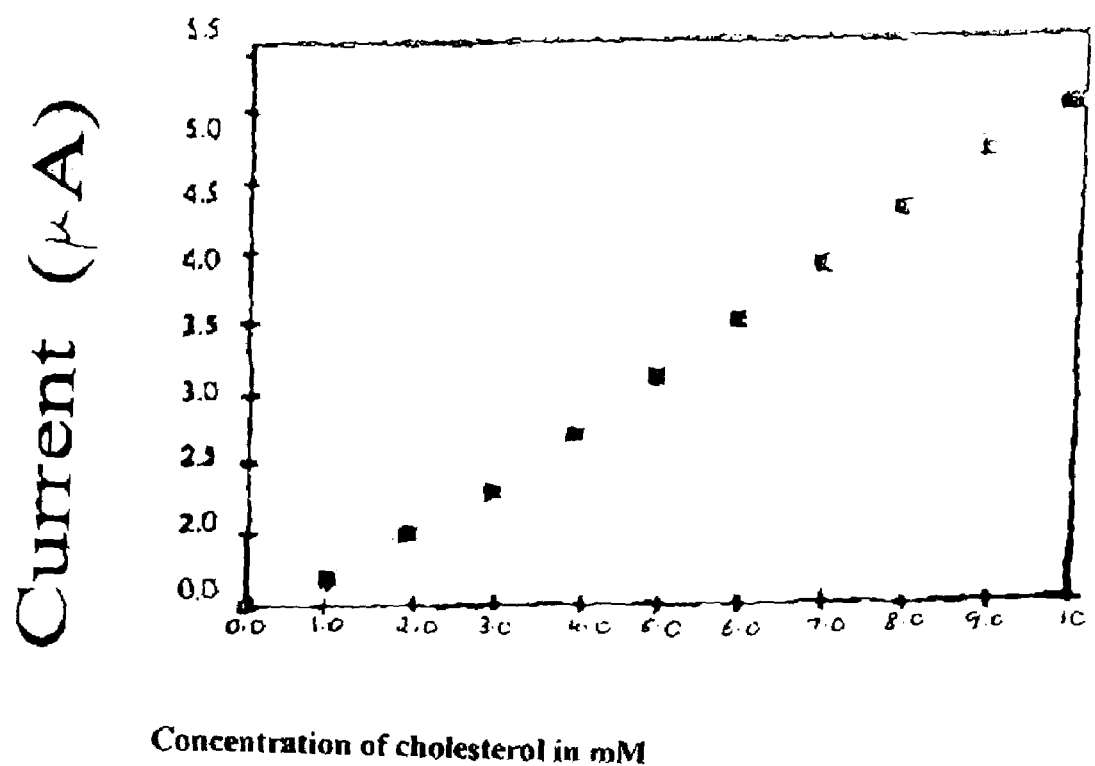

"Redox Mediators and their Application in Amperometric Sensors," Turner et al., pp. 131-138 and 140 in Analytical Uses of immobilized biological Compounds for Detection, Medical and Industrial Uses, 1988 by D. Reidel Publishing.*

Brahim et al. ("Amperometric determination of cholesterol in serum using a biosensor of cholesterol oxidase contained within a polypyrrole-hydrogel membrane," Analytica Chimica Acta 448 (2001) 27-36).*

Niu et al. ("Reagentless mediated biosensors based on polyelectrolyte and sol-gel derived silica matrix," Sensors and Actuators B 82 (2002) 250-258).*

CAPLUS abstract of Dong (CN 1118376 A) Mar. 13, 1996.*

CAPLUS abstract of Watanabe et al. (WO 2002057767 A1) Jul. 25, 2002.*

Kumar et al. "Co-Immobilization of Cholesterol Oxidase and Horseradish Peroxidase in a Sol-gel Film", Analytica Chimica Acta, vol. 414, No. 1-2, Jun. 1, 2000, pp. 43-50, XP002251005.

Wang, "Sol-gel Materials for Electrochemical Biosensors", Analytica Chimica Acta, vol. 399, No. 1-2, Nov. 8, 1999, pp. 21-27, XP002251371.

Chaubey et al, "Mediated Biosensors", Biosensors & Bioelectronics, vol. 17, No. 6-7, Jun. 2002, pp. 441-456, XP002251006.

Liu et al. "A New Tyrosinase Biosensor Based on Tailoring the Porosity of $Al_2O_3$ sol-gel to co-immobilize Tyrosinase and the Mediator", Analytica Chimica Acta, vol. 407, No. 1-2, Feb. 29, 2000, pp. 87-96, XP002251007.

Li et al, "Mediated Amperometric Glucose Sensor Modified by the sol-gel Method", Sensors And Actuators B. Elsevier Sequoia S.A., Lausanne, CH, vol. 40, No. 2-3, May 15, 1997, pp. 135-141, XP004088710.

Patent Abstracts Of Japan. vol. 011, No. 293 (P-619), Sep. 22, 1987 & JP 62 088952 A.

* cited by examiner

ENZYME ELECTRODE AND PROCESS FOR PREPARATION THEREOF

FIELD OF THE INVENTION

The present invention relates to a novel enzyme electrode useful for the determination of cholesterol in an aqueous solution. The present invention primarily also provides a process for the preparation of an enzyme electrode by coating an immobilized cholesterol oxidase (ChOx) and mediator on a silicate sol gel by microencapsulation.

BACKGROUND OF THE INVENTION

Cholesterol and its fatty acid esters are important compounds for human beings as they are components of nerve and brain cells and are precursors of other biological materials, such as bile acid and steroid hormones (P. L. Yeagle, Biology of Cholesterol, CRC Press: Its function and metabolism in biology and medicine Plenum: New York, 1972). Cholesterol determination in blood is clinically important for the diagnosis of heart diseases since accumulation of cholesterol and its fatty acid esters in blood due to excessive ingestion can be fatal (D. Noble, Anal. Chem., 1993, 65, 1037A-41A). The normal range of blood serum values extends from 3 to 6 mm for total cholesterol while in the hyperlipidamic condition the level can increases to 10 mM It is therefore desired to develop techniques that allow convenient and rapid determination of cholesterol.

Various methods have been employed in the art for stabilization and immobilization of enzymes within carbon paste or covalently liking it to the surface of glassy carbon electrode or immobilizing it within a polymer film for the preparation of enzyme electrode. In recent years, enzyme immobilization with the retention of enzyme activity within a sol-gel matrix has become a potential tool for development of new biosensors. Avnir et al disclose the immobilization of organic compounds in inorganic supports by introducing the organic compound with a polymerization precursor [J. Phys. Chem., 88 (1984), 5969]. Sol-gel processed materials are known for their use in development of ceramic films for conductive, optical, mechanical and electro-optic applications [Brinker, C. J., and Scherer, G. W., Sol-Gel Science, Academic Press, New York, (1989), Klein, L. C., Annu. Rev. Mater. Sci., 23 (1993) 437]. Braun et al report that alkaline phosphatase retains its activity when immobilized in a sol-gel matrix [Mater. Lett., 10 (1990) 1]. There is disclosure in the art of the immobilization of enzymes including glucose oxidase within a sol-gel matrix [Yamanaka et al, Chem. Mater. 4 (1992) 495; Shtelzer et al, Biochem. Biotechnol., 19 (1994) 293; Narang et al, Anal. Chem., 66 (1994) 3139].

Audebert and Sanchez report the construction of a ferrocene mediated sol-gel biosensor using a two stage sol-gel preparation method based on TMOS and commercial colloidal silica of varying particle size [Chem. Mater. 5 (1993) 911]. According to this literature reference, more than 80% of the glucose oxidase retains its activity in the gel and the Faradic response of the electrode agrees with theoretical calculations based on this activity. Lev et al disclose the use of sol-gel derived composite silica-carbon electrodes and claim the dual advantage of both the porosity and rigidity of the silica matrix and the electrical conductivity of the graphite [Anal. Chem., 66 (1994) 1747]. In this disclosure, glucose oxidase is first adsorbed on the surface of the carbon powder and then used for the preparation of the sol-gel film on a glassy carbon electrode. Kurokawa et al report a similar method where fabricated glucose oxidase doped sol-gel composite is made of various composite fibers such as cellulose or titanium propoxide [Biotechnol. Bioeng., 42 (1993) 394; Biotechnology 7 (1993) 5].

The co-immobilisation of cholesterol oxidase and horse radish peroxidase in a sol gel film is disclosed for example in Analytica Chimica Acta Vol 414, 23 pp, 2000, the method of this disclosure comprises physical adsorption, physically entrapped sandwich and the use of microencapsulation technique for the immobilization of cholesterol and horse radish peroxidase on tetra ortho silicate derived sol gel films. The response time for cholesterol estimation is more than 100 minutes. A response time of 50 seconds was observed amperometrically with a physically entrapped enzyme sandwich sol gel film. Further the enzyme electrode is reported to be stable for a period of 8 weeks only.

Biosensors used in the art suffer from several drawbacks in terms of stability and shorter shelf life. Several have reported methods of immobilization of biorecognition elements for use in chemical sensing researchers [R. F. Taylor, Protein Immobilizing Fundamentals and Applications: Marcel Dicker, New York (1975) Chapter 8, 263-303 and H. H. Weetall, Immobilized Enzyme; Antigen, Antibodies and Peptides Preparation and Characterization: Marcel Dicker, New York (1975) Chapter 6, 263-303]. The methods reported in literature can generally be classified into one of the following categories (1) physisorption (2) covalent attachment or (3) entrapment, among which physisorption is the simplest immobilization approach.

Several disadvantages arise with these methods of immobilization such as problems associated with the large size of the biorecognition elements (e.g. proteins and enzymes). Physisorption produces a range of biorecognition element orientations and apparent biding affinities. Besides physisorption generally leads to a population of biorecognizing elements that is completely unresponsive to target analyte. The immobilized species is completely unresponsive to target analyte. The immobilized species will often leach/desorb from sensing interface because there are no covalent bonds. Covalent schemes generally lead to more stable and uniform (interim of biorecognition orientation) interface and enzyme leaching is minimized. Unfortunately covalent attachment can involve one or more chemical transformation and tends to be time consuming and can be costly.

U.S. Pat. No. 6,342,364 provides a sensor that electrochemically determines cholesterol in low density lipoprotein by only one feed of a sample. The sensor has: an electrode system that is mounted on an electrically insulating base plate and includes at least a working electrode and a counter electrode; an enzyme layer formed on the base plate with the electrode system; and a reagent layer that is arranged before the enzyme layer in a sample solution supply path to the electrode system. The enzyme layer includes at least an oxidoreductase and an electron mediator. The reagent layer includes a reagent that depresses reactivity of cholesterol in lipoproteins other than the low density lipoprotein with the oxidoreductase, for example, a reagent that attaches to lipoproteins other than the low density lipoprotein to form a water-soluble complex. However, the shelf life of this sensor is too low.

U.S. Pat. No. 6,214,612 discloses a cholesterol sensor for quantitative determination of cholesterol is provided containing an electrode system and a reaction reagent system. The electrode system contains a measuring electrode such as a carbon electrode and a counter electrode, and the reaction reagent system contains cholesterol dehydrogenase, nicotinamide adenine dinucleotide and an oxidized electron mediator. Electron mediators include ferricyanide, 1,2-naphthoquinone-4-sulfonate, 2,6-dichlorophenol indophenol, dimethylbenzoquinone, 1-methoxy-5-methylphenazinium sulfate, methylene blue, gallocyanine, thionine, phenazine methosulfate and Meldola's blue. Diaphorase, cholesterol esterase and a surfactant may also be present. The electrode system is on an insulating base plate, and the base plate has a covering member containing a groove that is a sample supplying channel which extends from an end of the base plate to the electrode system. A reaction layer containing the reagent system in dry form and a layer of a hydrophilic polymer is provided on the base plate or the covering member, or on both the electrode system and covering member so as to be exposed to the sample supplying channel. During operation, the electron mediator is reduced in conjunction with oxidation of cholesterol in a sample by cholesterol dehydrogenase, and an amount of current required to electrochemically re-oxidize the electron mediator is directly proportional to a quantity of cholesterol present in the sample. However, the sensor has a low shelf life and also potentially shows leaching of both the mediator and the enzyme.

U.S. Pat. No. 6,071,392 discloses a cholesterol sensor which comprises an electrode system having a measuring electrode and a counter electrode formed on an electrically insulating base plate, an electrode coating layer for covering the electrode system and a reaction reagent layer formed on or in the vicinity of the electrode coating layer, wherein the reaction reagent layer comprises at least an enzyme for catalyzing cholesterol oxidation, an enzyme having a cholesterol ester hydrolyzing activity and a surfactant, the electrode coating layer comprises at least one selected from the group consisting of water-soluble cellulose derivatives and saccharides and is contained at such a concentration that imparts sufficient viscosity to a sample solution for enabling it to hinder invasion of said surfactant into said electrode system when said electrode coating layer is dissolved in said sample solution supplied to said sensor. The sensor of this patent is aimed at eliminating impairment of sensor response due to electrode degeneration caused by invading surfactant into the electrode system. While the response time is stated to be low, the shelf life is again not high due to potential enzymatic leaching.

U.S. Pat. No. 6,117,289 discloses a cholesterol sensor which comprises an electrode system composed of at least a measuring electrode and a counter electrode and disposed on an electrically insulating base plate and a reaction layer formed on or in the vicinity of the electrode system. The reaction layer contains cholesterol esterase for catalyzing the conversion of cholesterol ester into cholesterol, cholesterol oxidase and a surfactant. The response time was up to nine minutes. Additionally the presence of a surfactant can result in electrode degradation.

Electrochemically polymerised conducting polymers have also received considerable attention over the last two decades. The remarkable switching capacity of these materials between the conducting oxidised (doped) and the insulating reduced (undoped) state is the basis of many applications. For example, polyconjugated conducting polymers have been proposed for biosensing applications because of advantageous characteristics such as direct and easy deposition on the sensor electrode by electrochemical oxidation of monomer, control of thickness by deposition of charge and redox conductivity and polyelectrolyte characteristics of the polymer useful for sensor applications.

It is therefore highly desirable to develop biosensors that allow conventional and rapid determination of cholesterol.

OBJECTS OF THE INVENTION

The main object of the present invention is to provide a novel sol gel based enzyme electrode useful for the estimation of cholesterol in aqueous medium.

Another object of the invention is to provide a process for the preparation of a novel enzyme electrode, which allows an accurate and rapid estimation of cholesterol in solution.

Yet another object of the present invention is to provide an enzymatic stable, cost-effective high sensitive enzyme electrode.

Still another object of the present invention is to provide an enzyme electrode, which provides an accurate measurement of cholesterol within a short time period of 30 seconds.

It is yet another object of the invention to provide a novel sol gel based enzyme electrode which is reusable at least five times.

SUMMARY OF THE INVENTION

Accordingly the present invention relates to an enzyme electrode useful for estimation of cholesterol in aqueous medium, said electrode comprising:
i. An electrically conductive base plate,
ii. a film of sol gel derived material deposited thereon,
iii. said sol gel derived material of step b) being microencapsulated cholesterol oxidase with an electron mediator, said enzyme electrode showing zero leaching of the encapsulated enzyme and of the electron mediator, a response time of 30 seconds, being reusable at least five times and a shelf life of six months.

In another embodiment of the invention the electrically conductive base plate used is selected from indium tin oxide coated glass plate and a silver coated non-conducting polymer surface.

In still another embodiment of the invention, the non-conducting polymer surface used is selected from a film and a sheet.

In a further embodiment of the invention non-conducting polymer surface used is selected from the group consisting of polyacrylamide, polyvinyl chloride and polyethylene.

In another embodiment of the present invention the sol material used is silica sol.

In yet another embodiment of the invention, the silica sol used is selected from tetraethyl orthosilicate and tetramethyl orthosilicate.

In another embodiment of the invention the electron mediator used is selected from potassium ferricyanide, ferrocene and Prussian blue.

In a further embodiment of the invention the enzyme electrode has a sensitivity of 0.4 volt.

In another embodiment of the invention the strength of cholesterol oxidase used is in the range of 3-5 IU per 1×1 $cm^2$ of surface area.

In a further embodiment of the invention the enzyme electrode works at a pH in the range of 6.5-7.2.

The present invention also relates to a process for the preparation of enzyme electrode useful for estimation of cholesterol in aqueous medium, which comprises the steps of:
a. preparing a silicate solution by known methods,
b. immobilizing an enzyme cholesterol oxidase and an electron mediator by slowly adding 0.05-0.1 M phosphate buffer containing 3-5 IU of cholesterol oxidase and about 0.01M of electron mediator on to the above said silicate solution of step a), c. allowing the resultant mixture to stand till the complete encapsulation of enzyme and mediator by observing turbidity, d. spreading the resultant turbid mixture on a conductive base plate by conventional methods, e. drying the conductive base plate with the spread mixture for at least one day at a temperature in a range of 25-30° C. to obtain the enzyme electrode.

In an embodiment of the invention the silicate sol used is selected from tetraethyl orthosilicate and tetramethyl orthosilicate.

In another embodiment of the invention, the phosphate buffer used has a pH in a range of 6.5-7.2.

In yet another embodiment of the invention the process of preparation of enzyme electrode is a single step process.

BRIEF DESCRIPTION OF THE ACCOMPANYING DRAWING

FIG. 1 shows the response of the enzyme electrode as a function of the concentration of cholesterol solution.

DETAILED DESCRIPTION OF THE INVENTION

The present disclosure essentially involves the stages of preparation of sol and simultaneous addition of mediator in buffer solution added to sol along with the cholesterol oxidase enzyme. The mixture of sol and immobilized enzyme is allowed to stand till the complete encapsulation of the enzyme is achieved. This stage is judged by observing the onset of turbidity of the moisture. Once the mixture turns turbid, it is usable for deposition on a substrate to prepare the desired electrode. The spread mixture when allowed to dry for long time of about 24 hours at a temperature of about 25-30° C., results in a thin film which has the cholesterol sensing property.

The preparation of sol is accomplished by using preferably tetraethyl silicate in pure water and HCl. However tetramethyl silicate may also be used. The water used in the preparation of the sol is preferably pure water and more preferably a deionized water of more than 15 Mohms. The preparation of sol maybe accomplished by any conventional known means known to a person skilled in the art. For example, a stock sol-gel solution is prepared by mixing 4.5 ml of tetra ethyl orthosilicate (TEOS), 1.4 ml of $H_2O$ and 100 ul of 0.1 M HCl ill a glass vial. The mixture was stirred regularly until a clean solution was obtained. This solution was used throughout the experiment and was diluted as required. Specific casting solution was prepared by mixing 0.5 ml of the stock solution with 0-0.2 ml of deionized water.

The next critical step involves preparation of the sol gel containing the immobilized cholesterol oxidase enzyme. The speciality in this is the simultaneous encapsulation and immobilization of the enzyme while the mediator is being added gradually to the sol with the buffer containing the enzyme. The enzyme used is cholesterol oxidase of a concentration in a range of 3-5 IU per square cm of surface area. The mediator used is preferably potassium ferricyanide. For the immobilization of cholesterol oxidase (ChOx) 80 μl of stock solution was added to 20 μl of 0.01M potassium ferricyanide solution made in 0.1 M phosphate buffer (pH 7.0) containing 3U of ChOx for simultaneous entrapment of the enzyme and potassium ferricyanide as a mediator in the growing hydrolyzed gel forming silica network. The solution was kept aside until the enzyme and mediator was encapsulating completely with in the growing network.

Once the sol gel containing the immobilized and microencapsulated enzyme is prepared it is ready for use for deposition as a film on a conducting substrate. The conducting substrate may be a glass plate coated with a conducting film like Indium Tin Oxide (ITO) or may also be any other substrate like a polymer film or a sheet. These may have a deposited silver film for use as a conducting surface for the deposition of film of the sol gel containing encapsulated enzyme. Prior to film casting indium tin oxide (ITO) coated glass plates were first treated with $HNO_3$, for about 2 hrs and were subsequently rinsed thrice with Millipore water. The glass slides were finally washed with n-propanol prior to film coating technique. The film may be prepared by any conventional means known to a person skilled in the art and is preferably kept in air for drying at a temperature in a range of 25-30° C. Films of varying thickness doped with ChOx were then cast onto the ITO glass using the water sol-gel dilution scheme. The film was dried at 25° C. and was stored at 4° C.

A standard cholesterol solution was prepared by dissolving 3 mg of Cholesterol in 12.8 ml of propan-2-ol and was mixed with 5.85 ml of Triton X-100 surfactant. After homogenization the volume was made up to 10 ml with 0.1M phosphate buffer (pH 7.0) and thermostat at 35° C. This standard solution was further diluted with water to make different cholesterol solutions.

The characteristics of the enzyme coated substrate are measured using Amperometric response studies using the standard cholesterol solution prepared above. Amperometric techniques are well known to a person skilled in the art. In this method, essentially a three-electrode cell configuration is used. The electrodes used are the working electrode i.e. the enzyme electrode of the present invention. Typically the enzyme electrode was made on an ITO coated glass. The second electrode is the reference electrode of Ag/AgCl. In actual measurement, cholesterol solution of strength varying between 0.5-10 mM in a phosphate buffer of pH of 7.0 was used with the two electrodes as described above. The current due to enzymetrically produced $H_2O_2$ was measured every 100 seconds. Typically a response time of seconds was measured for a concentration of The reaction giving rise to current is due to the following scheme Cholesterol+$O_2$→Δ-Cholesten-3-one+$H_2O_2$

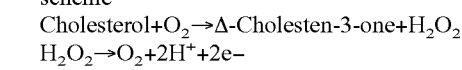

The results of the experiments are shown in FIG. 1. In order to check if addition of any interfering agents in cholesterol, like glucose or ascorbic acid, will have any deleterious effect on the response of the enzyme electrode, the experiment was repeated with cholesterol solution mixed with the interfering agents. It was found that these interfering agents did not show any effect on the response to the enzyme electrode.

In an attempt to improve the shortcomings of the prior art disclosures of cholesterol measurement, the bio molecules are immobilized in sol-gel and have comparatively enhanced shelf lives. This is because of fact that (i) a variety of enzymes may be encapsulated in sol-gel matrices giving optical transparent glasses (ii) the enzymes are remarkable stable in such matrices (iii) these enzymes undergo characteristics reversible reaction in sol-gel glasses and (iv) spectroscopic changes occurring in sol-gel glasses can readily be quantified by optical spectroscopy. The sol-gel technique is advantageous since little or no heating is required. Such enzyme molecules become entrapped in the covalent network rather then being chemically bound to the inorganic matrix as chemical bonding of the substrate may perturb the activity of the molecule. The fine pore network in dried glass (<10 nm) does not scatter visible radiation and allows the diffusion of small molecules onto the electrode surface. Porous inorganic xerogel such as tetra ethyl orthosilicate (TEOS) derived sol-gels are particularly attractive matrices for electrochemical biosensors since they combine physical rigidity, negligible swelling in aqueous solution, chemical inertness and thermal stability. These biosensors in principle have sensitivity and rapid response time and are also free from the problem of any detrimental effects on enzyme activity.

Another significant advantage observed over the prior art enzyme electrodes is that there is zero leaching of the enzyme and the mediator. The electrode of the invention also has a reduced response time of 30 seconds and is reusable. It is also observed that the shelf life of the electrode is enhanced and is about six months at ambient temperature of 25-30° C.

The inventive step of the present invention resides in the immobilization of the enzyme cholesterol oxidase (ChOx) and electron mediator in silicate sol-gel by micro-encapsulation technique and depositing the above said microencapsulated enzyme and mediator sol-gel film onto a conducting indium tin oxide (ITO) coated glass plate for the preparation of an enzyme electrode useful for the determination of cholesterol in solution.

The following examples are given by the way of illustration and therefore should not be constructed to limit the scope of the present invention in any manner.

EXAMPLE 1

Enzyme Activity Measurements

A solution of 0.05 cm$^3$ of 6 mm cholesterol dissolved in propane-2-ol and volume of 3 cm$^3$ of 0.1 M phosphate buffer (pH 7.0) were mixed and kept in a thermostat at 35° C. The ChOx immobilized sol-gel film coated ITO glass plate was immersed and incubated for 2 minute, the plate was removed and the absorbance of the solution was measured at 240 nm using a double beam spectrometer to determine the cholesterol produced by the enzymatic reaction. The apparent enzyme activity (U cm$^3$) was evaluated by the following procedure based on the difference in absorbance before and after incubation of the enzyme immobilized sol-gel glass plate.

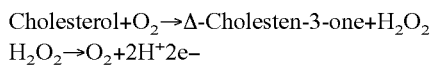

Where A is a deference in absorbance before and after incubation, V is the total volume (3.05 cm3), $\epsilon$ is the millimolar extinction coefficient of cholesterol (12.2), t is the reaction time (min) and s is the surface area (cm$^3$) of sol-gel film. One unit of enzyme activity (U cm$^3$) is defined as the activity that results in the production of 1 ul mol of cholesterol per minute. The enzyme activity measurements were made on the enzyme (ChOx/HRP) immobilized sol-gel film. No enzyme (ChOx/HRP) leaching was observed from the enzyme immobilized sol-gel film.

EXAMPLE 2

Electromechanical estimation of cholesterol containing interfering reagents by using cholesterol oxidase immobilized sol-gel-ITO(ChOx/sol-gel/ITO) electrode.

Cyclic Voltametery Studies

When cholesterol comes in contact with enzyme electrode containing ChOx immobilized in a TEOS derived sol-gel film the following enzymatic and electrochemical reaction occurs.

Cholesterol+$O_2$→$\Delta$-Cholesten-3-one+$H_2O_2$ $H_2O_2$→$O_2$+2H$^+$2e−

The oxidation current for $H_2O_2$ is recorded as the sensor response in the amperometric biosensor. Owing to the direct immobilization of the enzyme, the sensor properties such as time and sensitivity are the reflection of the immobilized enzyme. The cyclic voltammetry experiments were carried out in 0.1 M phosphate buffer (pH 7.0) containing different concentration of cholesterol (0.5 mM to 10 mM) using enzyme immobilized sol-gel film cast on ITO glass plate as a working electrode a Ag/AgCl reference electrode and a Pt wire as a counter electrode. The above experiment was conducted in the absence and in the presence of 0.1 mM ascorbic acid and 0.5 mM glucose as interfering reagents. The cyclic voltametry shows an oxidation peak at 750 mV which keeps on increase in anodic current with an increase in concentration from 0.5 mM to 10 mM cholesterol. The rise is attributed to the direct oxidation of $H_2O_2$ on the surface of the ITO coated glass plate. However the oxidation peak at 0.75V shifts anodically by 150 mV to 0.9 V Vs Ag/AgCl with increase in anodic current in the presence of 0.1 mM ascorbic acid. The presence of 0.5 mM glucose in the cholesterol solution (1 mM) also shows an increase in anodic current but does not show any significant effect on the oxidation potential of $H_2O_2$, thereby showing that the presence of both 0.1 mm ascorbic acid 0.5 mm glucose in cholesterol have a significant effect on the observed anodic current.

EXAMPLE 3

Amperometric Response Studies

A three electrode cell configuration similar to the one used in cyclic voltameteric experiment was used for the amperometric determination of cholesterol in phosphate buffer (pH 7.0). The working electrode (comprising cholesterol oxidase ChOx immobilized sol-gel at ITO glass) was polarizing at 0.9V versus Ag/AgCl and amperometric response to cholesterol (0.5-10 mM) was measured by using amperometric calibration for enzymematically produced $H_2O_2$. The current was monitored every 100 sec after dispensing different concentration of cholesterol solution (2 mM-10 mM) into the cell. A maximum current of 5.0 uA was obtained for 10-mM cholesterol above which no significant change in current could be observed. The response time to total cholesterol was found to be 90 sec.

EXAMPLE 4

Electrochemical estimation of cholesterol using cholesterol oxidase and potassium ferricyanide immobilized sol-gel indium tin oxide (ChOx/Fe$^{3+}$/sol-gel/ITO) as electrode and with influence of interfering reagents such as ascorbic acid (0.1 mM) and glucose (0.5 mM)

Cyclic Voltametery Studies

The cyclic voltammetry experiments were carried out in 0.1 M phosphate buffer (pH 7.0) containing different concentration of cholesterol using enzyme cholesterol oxidase and potassium ferricyanide immobilized sol-gel indium tin oxide (ChOx/Fe$^{3+}$/sol-gel/ITO) film as a working electrode, a Ag/AgCl reference electrode and a Pt wire as a counter electrode. The following reactions occur Cholesterol+ChOx→Cholestenone+ChOx$_{red}$
ChOx$_{red}$+Fe$^{3+}$(ferricyanide)→ChOx+Fe$^{2+}$ (ferrocyanide)

$$Fe^{2+}(\text{ferrocyanide}) \xrightarrow{0.4\,V} Fe^{3+}(\text{ferricyanide}) + e- (\text{at electrode})$$

The oxidation current is recorded as the sensor response in the amperometric biosensor. Owing to the direct immobilization of the enzyme, the sensor properties such as time and sensitivity are the reflection of the immobilized enzyme. An oxidation peak observed earlier in Example 2 at 0.9V vs. Ag/AgCl when enzyme immobilized sol-gel film without mediator was used as an electrode now shifts 300 mV cathodically and is observed at 0.4V versus Ag/AgCl, which increases with increase in cholesterol concentration (2 to 10 mM). The presence of 0.1 mM ascorbic acid and 0.5 mM glucose in cholesterol solution does not show any significant effect on the oxidation potential.

EXAMPLE 5

Amperometric Response Studies

A three electrode cell configuration similar to the one used in cyclic voltameteric experiment has been used for the amperometric determination of cholesterol in phosphate buffer (pH 7.0). The working electrode (comprising cholesterol oxidase ChOx immobilized sol-gel at ITO glass) was polarized at 0.4V versus Ag/AgCl and amperometric response to cholesterol of concentration varying from 2 mM to 10 mM was measured. The current was monitored every 100 sec after different concentration of cholesterol solution (2 mM to 10 mM) into the cell (FIG. 1). The anodic current measured in 6 mM cholesterol solution (1 mL) at ChOx/Fe$^{3+}$/sol-gel/ITO polarized at 0.4 V yields the stead the state in 30 seconds and this response to cholesterol solution was reproducible to within 5%. The lower detection limit of cholesterol was found amperometrically to be 0.5 mM.

The Main Advantages of the Present Invention are:
1. Enzymatic electrodes prepared by the invention shows negligible enzyme leaching.
2. The enzyme electrode prepared shows fast response to cholesterol in solution
3. The enzyme electrode prepared is stable for a longer time.
4. The enzyme electrode prepared is highly sensitive to cholesterol.

We claim:
1. A process for the preparation of enzyme electrode useful for estimation of cholesterol in aqueous medium, which comprises the steps of:
   a. preparing a silicate solution,
   b. immobilizing an enzyme cholesterol oxidase and an electron mediator by slowly adding 0.05-0.1 M phosphate buffer containing 3-5 IU of cholesterol oxidase and about 0.01 M of electron mediator to the above said silicate solution of step a),
   c. allowing the resultant mixture to stand till the complete encapsulation of enzyme and mediator by observing turbidity,
   d. spreading the resultant turbid mixture on an electrically conductive base plate,
   e. drying the electrically conductive base plate with the spread mixture for at least one day at a temperature in a range of 25-30° C. to obtain the enzyme electrode comprising:
      i. an electrically conductive base plate,
      ii. a film of sol gel derived material deposited thereon,
      iii. said sol gel derived material of ii) being microencapsulated cholesterol oxidase with an electron mediator,
      said enzyme electrode showing zero leaching of the encapsulated enzyme and of the electron mediator, a response time of 30 seconds, an amperometric linear response to cholesterol in the range of 1-8 mM, being reusable at least five times and a shelf life of six months.
2. A process as claimed in claim 1 wherein the silicate solution is selected from the group consisting of tetraethyl orthosilicate and tetramethyl orthosilicate.
3. A process as claimed in claim 1 wherein the phosphate buffer used has a pH in a range of 6.5-7.2.
4. A process as claimed in claim 1 wherein the electrically conductive base plate is selected from the group consisting of indium tin oxide coated glass plate and silver-coated non-conducting polymer surface.
5. A process as claimed in claim 4 wherein the non-conducting polymer surface is selected from the group consisting of a film and a sheet.
6. A process as claimed in claim 5 wherein the non-conducting polymer surface is selected from the group consisting of polyacrylamide, polyvinyl chloride and polyethylene.
7. A process as claimed in claim 1 wherein the electron mediator is selected from the group consisting of potassium ferricyanide, ferrocene and Prussian blue.
8. A process as claimed in claim 1 wherein the strength of cholesterol oxidase is in the range of 3-5 IU per 1×1 cm$^2$ of sol-gel surface area.

* * * * *